US010125349B2

(12) United States Patent
Pijuan Galito et al.

(10) Patent No.: US 10,125,349 B2
(45) Date of Patent: Nov. 13, 2018

(54) METHOD FOR CELL CULTURE

(71) Applicant: GE Healthcare Bio-Sciences AB, Uppsala (SE)

(72) Inventors: Sara Pijuan Galito, Uppsala (SE); Christoffer Tamm, Uppsala (SE); Cecilia Anneren, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/780,873

(22) PCT Filed: Mar. 27, 2014

(86) PCT No.: PCT/SE2014/050373
§ 371 (c)(1),
(2) Date: Sep. 28, 2015

(87) PCT Pub. No.: WO2014/158089
PCT Pub. Date: Oct. 2, 2014

(65) Prior Publication Data
US 2016/0053225 A1    Feb. 25, 2016

(30) Foreign Application Priority Data
Mar. 28, 2013  (SE) .................... 1350400

(51) Int. Cl.
C12N 11/14     (2006.01)
C12N 9/76      (2006.01)
C12N 5/0735    (2010.01)
C12N 5/074     (2010.01)

(52) U.S. Cl.
CPC ......... *C12N 5/0606* (2013.01); *C12N 5/0696* (2013.01); *C12N 2501/40* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 6,448,054 B1 * | 9/2002 | Poznansky | C07K 14/521 424/184.1 |
| 9,714,415 B2 | 7/2017 | Galito | |
| 2007/0010008 A1 * | 1/2007 | Tseng | C12N 5/0605 435/325 |
| 2007/0128719 A1 | 6/2007 | Tseng et al. | |
| 2007/0160594 A1 | 7/2007 | Filvaroff et al. | |
| 2012/0219737 A1 | 8/2012 | Sugino et al. | |
| 2016/0340646 A1 | 11/2016 | Pijuan Galito et al. | |
| 2017/0022471 A1 | 1/2017 | Pijuan Galito et al. | |
| 2017/0096642 A1 | 4/2017 | Pijuan Galito et al. | |

FOREIGN PATENT DOCUMENTS

| | | |
|---|---|---|
| EP | 2978839 A1 | 2/2014 |
| JP | 2005501513 A | 1/2005 |
| WO | 9640866 A1 | 12/1996 |
| WO | 2008002329 A2 | 1/2008 |
| WO | 2014/158089 A1 | 10/2014 |

OTHER PUBLICATIONS

West et al., "Angiogenesis Induced by Degradation Products of Hyaluronic Acid", Science, vol. No. 228, pp. 1324-1326, Mar. 25, 1985.
Enghild et al., "Analysis of Imter-a-trypsin Inhibitor and a Novel Trypsin Inhibitor, Pre-a-trypsin Inhibitor, from Human Plasma", The Journal of Biological Chemistry, vol. No. 264, Issue No. 27, pp. 15975-15981, Sep. 25, 1989.
Chen et al., "Identification of a Factor in Fetal Bovine Serum That Stabilizes the Cumulus Extracellular Matrix", The Journal of Biological Chemistry, vol. No. 267, Issue No. 17, pp. 12380-12386, Jun. 15, 1992.
Jiang et al., "Involvement of a Protein Distinct from Transcription Enhancer Factor-1 (TEF-1) in Mediating Human Chorionic Somatomammotropin Gene Enhancer Function through the GT-IIC Enhanson in Choriocarcinoma and COS Cells", The Journal of Biological Chemistry, vol. No. 270, Issue No. 23, pp. 13906-13915, Jun. 9, 1995.
Trochon et al., "Evidence of Involvement of Cd44 in Endothelial Cell Proliferation, Migration and Angiogenesis In Vitro", International Journal of Cancer, vol. No. 66, pp. 664-668, 1996.
Wisniewski et al., "TNF/IL-1-Inducible Protein TSG-6 Potentiates Plasmin Inhibition by Inter-cw-Inhibitor and Exerts a Strong Anti-Inflammatory Effect In Vivo", The Journal of Immunology, vol. No. 156, pp. 1609-1615, 1996.
Blom et al., "Structural Characterization of Inter-a-inhibitor Evidence for an Extended Shape", The Journal of Biological Chemistry, vol. No. 274, Issue No. 1, pp. 298-304, Jan. 1, 1999.
Pienimaki et al., "Epidermal Growth Factor Activates Hyaluronan Synthase 2 in Epidermal Keratinocytes and Increases Pericellular and Intracellular Hyaluronan", The Journal of Biological Chemistry, vol. No. 276, Issue No. 23, pp. 20428-20435, Jun. 8, 2001.
Itano et al., "Abnormal accumulation of hyaluronan matrix diminishes contact inhibition of cell growth and promotes cell migration", Proceedings of the National Academy of Sciences, vol. No. 99, Issue No. 6, pp. 3609-3614, Mar. 19, 2002.
Toole et al., "Hyaluronan and Tumor Growth", American Journal of Pathology, vol. No. 161, Issue No. 3, pp. 745-747, Sep. 2002.

(Continued)

*Primary Examiner* — Maria Marvich
(74) *Attorney, Agent, or Firm* — Wood IP LLC

(57) ABSTRACT

A method for stem or progenitor cell culture. More precisely, the invention relates to a method for cell culture using one or more IαI (inter-alpha trypsin inhibitor or Inter-alpha inhibitor) protein(s) or part(s) thereof as a component in a cell culture media or a coating on a cell culture surface material. Furthermore the invention relates to a cell culture media and a cell culture coating/matrix provided with one or more IαI proteins(s) or part(s) thereof.

20 Claims, 8 Drawing Sheets

(56) References Cited

OTHER PUBLICATIONS

Baier et al., "Photocrosslinked Hyaluronic Acid Hydrogels: Natural, Biodegradable Tissue Engineering Scaffolds", Biotechnology and Bioengineering, vol. No. 82, Issue No. 5, pp. 579-589, Jun. 5, 2003.
Schoenfelder et al., "Expression of Hyaluronan Synthases and Corresponding Hyaluronan Receptors Is Differentially Regulated During Oocyte Maturation in Cattle", Biology of Reproduction, vol. No. 69, pp. 269-277, 2003.
Qi et al., "BMP4 supports self-renewal of embryonic stem cells by inhibiting mitogen-activated protein kinase pathways", PNAS, vol. No. 101, Issue No. 16, pp. 6027-6032, Apr. 20, 2004.
Josic et al., "Proteomic characterization of inter-alpha inhibitor proteins from human plasma", Proteomics, vol. No. 6, pp. 2874-2885, 2006.
Zhu et al., "The Role of the Hyaluronan Receptor CD44 in Mesenchymal Stem Cell Migration in the Extracellular Matrix", Stem Cells, vol. No. 24, pp. 928-935, 2006.
Watanabe et al., "A ROCK inhibitor permits survival of dissociated human embryonic stem cells", Nature Biotechnology, vol. No. 25, Issue No. 6, Jun. 2007.
Andang et al., "Optimized mouse ES cell culture system by suspension growth in a fully defined medium", Nature Protocols, vol. No. 3, Issue No. 6, pp. 1013-1017, 2008.
Moliner et al., "Mouse Embryonic Stem Cell-Derived Spheres with Distinct Neurogenic Potentials", Stem Cells and Development, vol. No. 17, pp. 233-243, 2008.
Ying et al., "The ground state of embryonic stem cell self-renewal", Nature, vol. No. 453, pp. 519-523, May 22, 2008.
Block et al., "Improving post-transfer survival of bovine embryos produced in vitro, Actions of insulin-like growth factor-1, colony stimulating factor-2 and hyaluronan", Advances in Bovine Reproduction and Embryo Technology, Theriogenology, vol. No. 76, pp. 1602-1609, 2011.
Chen et al., "Chemically defined conditions for human iPSCSC derivation and culture", Nature Methods, vol. No. 8, Issue No. 5, pp. 424-431, May 2011.
Tamm et al., "Regulation of mouse embryonic stem cell self-renewal by a Yes-YAP-TEAD2 signaling pathway downstream of LIF", Journal of Cell Science, vol. No. 124, pp. 1136-1144, 2011.
Tamm et al., "A Comparative Study of Protocols for Mouse Embryonic Stem Cell Culturing", Comparison of Protocols for E3 Cell Culturing, vol. No. 8, issue No. 12, pp. 1-10, Dec. 10, 2013.
Petrey et al., "Hyaluronan, A Crucial Regulator of Inflammation", Frontiers in Immunology, vol. 5, Article 101, Mar. 11, 2014, pp. 1-13.
Zhuo et al., "Inter-α-trypsin Inhibitor, A Covalent Protein-Glycosaminoglycan-Protein Complex", The Journal of Biological Chemistry, vol. 279, No. 37, 2004, pp. 38079-38082.
Evanko et al., "Hyaluronan-Dependent Pericellular Matrix", Adv Drug Deliv Rev., vol. 59, No. 13, 2007, pp. 1351-1365.
Sara Pijuan-Galito et al., "Human Serum-Derived Protein Removes the Need for Coating in Defined Human Pluripotent Stem Cell Culture," Nature Communications, Article published Jul. 13, 2016, 12 pages.
Stavros Garantziotis et al., "Inter-a-Trypsin Inhibitor Attenuates Complement Activation and Complement-Induces Lung Injury," The Journal of Immunology, 2007, 179, pp. 4187-4192.
R.D. Geisert et al., "Expression of Inter-a-Trypsin Inhibitor Heavy Chains in Endometrium of Cyclic and Pregnant Gilts," 2003, 126, pp. 621-627.
S. Zhang et al., "Constitutive Expression of Inter- -inhibitor (IaI) Family Proteins and Tumor Necrosis Factor-simulated Gene-6 (TSG-6) by Human Amniotic Membrane Epithelial and Stromal Cells Supporting Formation of the Heavy Chain-Hyaluronan (HC-HA) Complex," Journal of Biological Chemistry, vol. 287, No. 15, Apr. 6, 2012, pp. 12433-12444.
Elisa Messina et al., "Isolation and Expansion of Adult Cardiac Stem Cells From Human and Murine Heart," Circulation Research, American Heart Association, Inc., vol. 95, No. 9, Oct. 29, 2004, pp. 911-921.

\* cited by examiner

FIGURE 2

| IαI FAMILY PROTEINS | |
|---|---|
| Name | Combination of mature polypeptides |
| Bikunin | Free bikunin |
| IαI | HC1 + HC2 + bikunin |
| PαI | HC3 + bikunin |
| IαIH2,B | HC2 + Bikunin |
| IαIH1,2 | HC1 + HC2 (human, SHAP) |
| IαIH4P | Free H4P |
| Others | Intermediate and/or unknown species; IαIH1,B; IαIH4,B; p236 or IαIH2,3,B, HC5, etc. |

FIGURE 4

K02C human iPS cell line
Passage 67

E8 Media + VN peptide coating
Passage 16

E8 Media + IαI 20 μg/ml
Passage 14

METHOD FOR CELL CULTURE

FIELD OF THE INVENTION

The present invention relates to a method for cell culture. More precisely, the invention relates to a method for cell culture using one or more IαI (inter-alpha trypsin inhibitor or Inter-alpha inhibitor) protein(s) or part(s) thereof as a component in a cell culture media or a coating on a cell culture surface material. Furthermore the invention relates to a cell culture media and a cell culture coating/matrix provided with one or more IαI proteins(s) or part(s) thereof.

BACKGROUND OF THE INVENTION

Pluripotent stem (PS) cells e.g. embryonic stem (ES) cells and induced pluripotent stem (iPS) cells have the ability to maintain pluripotency during long-term culture and yet induce differentiation into multiple lineages and therefore potentially offer novel cell sources for e.g. basic research, toxicological screening, in vitro modeling of genetic disorders or therapeutic cell replacement. There are still many obstacles to overcome until these endpoints can be fully realized. For instance it will be necessary to find culture conditions that support safe, simple and robust derivation, growth, maintenance and large-scale expansion, while maintaining self-renewal, of these difficult to culture cells. Especially important is the need for methods for maintenance of human PS cells in vitro. These methods have to be good enough to maintain the population of cells without inducing mutagenesis, high levels of differentiation or loss of pluripotency.

Mouse ES cells are extensively used in basic research to e.g. study normal and pathological development and function and the knowledge obtained using these cells is often transferred to human systems. Most mouse ES (mES) cell lines used today are grown on pre-plated mitotically inactivated mouse embryonic fibroblast (MEF) feeder cells in media supplemented with selected batches of fetal bovine serum (FBS) and Leukemia inhibitory factor (LIF). The feeder cells provide a matrix that support mES cell attachment and secrete various growth factors that enhance the survival and propagation of mES cell growth whereas FBS provides hormones and essential nutrients, as well as altering the physiological/physiochemical properties of the medium. LIF drastically improves the derivation and maintenance of the pluripotency of mES cells. Some mES cell lines have been derived and adapted to grow feeder-free on 0.1% Gelatin coating (heterogeneous mixture of water-soluble proteins of high average molecular weight present in collagen and extracted from bovine skin) in serum and LIF containing media. Both these cell culture protocols have the shortcoming that many of their components (i.e. FBS, bovine serum albumin or BSA, gelatin) are not defined and are animal-derived. FBS, for instance, contains various growth factors and other undefined components that promote ES cell growth, but it has also been suggested to contain potential differentiation factors that can affect mES cell plating efficiency, growth and differentiation. Therefore FBS batches need to be pre-screened and ES-qualified to ensure that the net-effect of serum factors that sustain mES cell maintenance and growth outweighs the effects of differentiation-inducing factors. Feeders in their turn secrete a plethora of factors impossible to control and are a possible source of pathogenic contamination.

To improve control of what factors ES cells are actually subjected to, and to avoid interference from undesired factors, several newer and more defined protocols have been established. In 2003 it was shown that BMP4 could be efficiently used in combination with LIF for mES derivation and maintenance in serum- and feeder-free cultures (Qi, Li et al. 2004). In 2004, a chemically defined (the exact formulation is not described) synthetic knockout serum replacement (KOSR) was developed to replace serum. However, the KOSR cannot alone support mES single-cell culture in the absence of feeders. In 2008, it was shown that mES could be maintained in the absence of serum and feeder cells as free-floating spheres in a N2 supplemented medium with LIF and bFGF (basic fibroblast growth factor), herein named ESN2 medium (Andang, Moliner et al. 2008, Moliner, Enfors et al. 2008).

Recently, another defined media supplemented with two inhibitors, the mitogen-activated protein kinase (MAPK)/extracellular-signal-regulated kinase (ERK) kinase (MEK) inhibitor PD0325901 and the glycogen synthase kinase 3 (GSK3) inhibitor CHIR99021, added to a B27 and N2 supplemented medium (herein named 2i medium) was shown to maintain mES cell self-renewal without the addition of exogenous factors (Ying, Wray et al. 2008). Mouse ES cells cultured in 2i medium still respond to LIF, which enhances cloning efficiency and proliferation rates. A drawback with this culture protocol is that, in the absence of serum, the cells do not adhere to the tissue culture plate but instead grow as free-floating spheres (Tamm, Pijuan Galito et al. 2013); moreover, the growth rate of the mES cells is decreased.

Human PS (hPS) cells and their differentiated cells are most commonly cultured in the presence of surfaces or media containing animal-derived components, such as feeder layers (both mouse-derived, typically MEFs, and human-derived, typically human foreskin fibroblasts or HFFs), Matrigel® (soluble basement membrane extract of the Engelbreth-Holm-Swarm EHS tumor), knock out serum replacement (KOSR) and/or derivatives like BSA. These animal-derived reagents added to the culture environment expose the cells to potentially harmful viruses or other infectious agents, which could be transferred to patients or compromise general culture and maintenance of the hPS cells. In addition, such biological products are vulnerable to batch variations, immune responses and limited shelf-life, and the exposure of the cells to molecules from other species also creates changes that could create an immune response in the recipient, if the cells were to be used in cell therapy.

To date, several completely recombinant, xeno-free systems employing a chemically defined medium and a synthetic or defined surface have been described. The most recent success in human PS cells culturing was published in Nature methods in 2011 describing a chemically reduced and completely defined media, named E8 only containing 8 different chemical components, that could support hiPS cell derivation and further successful culture on Matrigel® or a vitronectin-based surface (Chen, Gulbranson et al. 2011). Even so, different cell lines and different laboratories obtain different results when using defined media, and the most widely used protocols are still the combination of Matrigel® and mTESR1® (which contains BSA, purified from FBS) for hPS cells; and Gelatin coating and media supplemented with FBS for mES cells. Moreover, hPS cells cannot be split as single cells if not in the presence of the ROCK-inhibitor molecule (i.e. Y-27632) (Watanabe, Ueno et al. 2007), and for routine passaging need to be split in clumps with a gentle dissociation technique, proving the crucial role of the extracellular environment for pluripotent stem cells.

There is still an urgent need to understand all the different components necessary for the growth and maintenance of undifferentiated, non-mutated, pluripotent stem cells. It is important to get the right combination of extracellular matrix (ECM) and media factors for an optimal maintenance, especially for the human PS cell lines, otherwise the cells show low attachment, survival and proliferation rates, as well as high levels of differentiation.

For the sake of cell survival and proliferation rate, current protocols for cell culture still use FBS or derivatives such as BSA in the cell culture media and, thus, there is still need of an improved serum free protocol that does not compromise the cells, the culture conditions or the pluripotency.

SUMMARY OF THE INVENTION

In the present invention there is a factor that promotes cell adhesion and long-term cell culture viability. More precisely, the present invention provides the novel use of Inter-alpha trypsin inhibitor (IαI) family proteins(s) or part(s) thereof, in particular HC2 (heavy chain 2), as a surface coating and/or media additive for cell adhesion and long-term culture, maintenance and growth of pluripotent stem cells for at least twenty passages, in the presence of partially or completely chemically defined media, without inducing noticeable differentiation or karyotype abnormalities.

Thus, in a first aspect the present invention provides a method for stem or progenitor cell culture, comprising addition of one or more protein(s) from the IαI (inter alpha trypsin inhibitor) protein family or part(s) thereof to a serum-free culture of cells. In an embodiment, the cells are stem cells. The addition according to an embodiment of the invention will promote self-renewal, attachment, survival and, in the case of PS cells, also pluripotency. The IαI proteins(s) or part(s) thereof are isolated from serum, produced as a recombinant protein, or synthesized chemically.

In an embodiment, the cells are adherent cells and in another embodiment the cells are PS (pluripotent stem) cells, and may be ES (embryonic stem) cells or iPS (induced pluripotent stem) cells. In one embodiment of the invention the cells are human.

In an embodiment, the IαI protein or part thereof is selected from IαI (IαIHC1, IαIHC2 and bikunin) or IαIH2, B. The heavy chains of the IαI proteins may be used, such as heavy chain 2 (HC2) from IαI.

In case of PS cells in an embodiment of the present invention, the cell culture is serum free.

In one embodiment the IαI proteins(s) or part(s) thereof are coated onto a cell culture surface, such as plastic, carriers, scaffolds, matrices or meshes, as a coating agent.

In another embodiment the IαI proteins(s) or part(s) thereof are added to a serum-free cell culture medium.

The concentration of the IαI proteins(s) or part(s) thereof is 0.1 μg/ml-200 μg/ml, particularly 2-100 μg/ml, more particularly 10-50 μg/ml culture medium or coating solution.

The method according to an embodiment of the present invention is suitable for cell culture during at least twenty passages without inducing differentiation or mutation of the cells. Following cell culture, the PS cells may be prepared/ provided for, for example: cell therapy, drug screening and toxicity assays.

In a second aspect, the invention provides a cell culture media comprising IαI protein(s) or part(s) thereof in a concentration of 0.1 μg/ml-200 μg/ml, particularly 2-100 μg/ml, more particularly 10-50 μg/ml. In an embodiment, the media is a serum free culture media.

In a third aspect, the invention provides a cell culture surface comprising a coating comprising IαI protein(s) or part(s) thereof in the above concentrations. The coating may take place overnight at 4° C., or 1-2 h at RT or 37° C., at a range of coating concentrations of 0.1 μg/ml-200 μg/ml, particularly 2-100 μg/ml, more particularly 10-50 μg/ml.

In a fourth aspect, the invention relates to use of IαI proteins, more particularly IαI or H2 for cell adhesion and renewal.

One or more of the various Inter-alpha trypsin inhibitor proteins(s) or part(s) will provide advantages over prior coating materials for culture of pluripotent stem cells, particularly undifferentiated, non-transformed, pluripotent stem cell lines. For example, the purification of Inter-alpha trypsin inhibitor proteins or parts thereof from human serum provides an animal-component free matrix and the usage of the side fraction from the commercial production of factor IX makes the process relatively simple and economic. However, the subparts of IαI could also be recombinantly expressed or synthesized chemically to make them completely defined.

The ability to culture undifferentiated cells on a chemically defined surface eliminates extra contamination components from animal serum components typical from complex medias. In addition, the batch to batch variation will be also reduced in comparison to serum and serum-derived additives such as serum (e.g., FBS), KOSR and BSA, as it would not rely on the proportional concentrations of different components. These and other advantages will be understood from the following description when read in conjunction with the enclosed figures.

BRIEF DESCRIPTION OF THE DRAWINGS

FIG. 2 shows an overview of the IαI family of proteins.

FIG. 4 shows attachment assay bright-field images of mES E14 cells grown 2i media on different coatings and/or with different media supplements.

DETAILED DESCRIPTION

Figure 1:
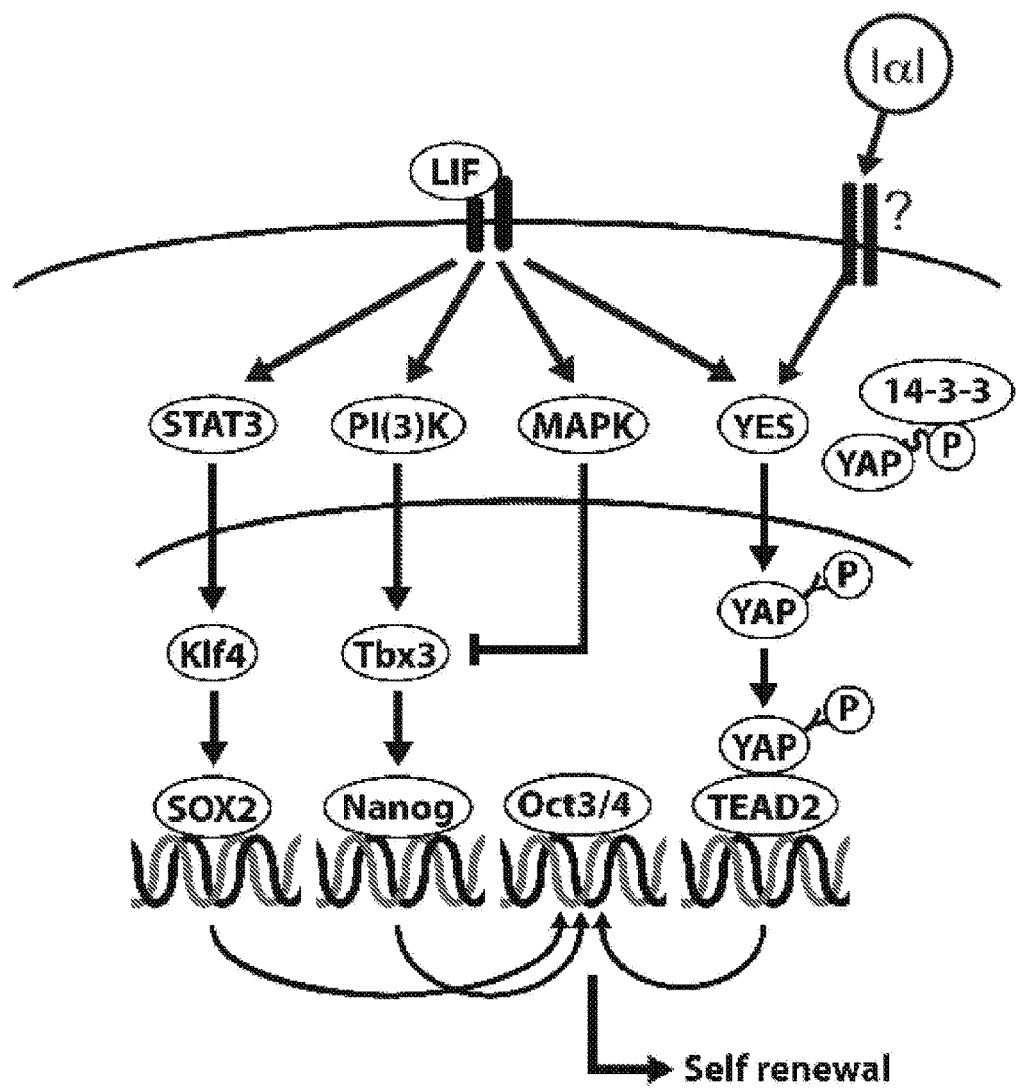
FIG. 1 is a schematic view of some of the self-renewal pathways in mES cells and shows the incorporation of IαI protein in TEAD2-Yes-YAP pathway.

It has been previously described that a novel kinase pathway is involved in the maintenance of self-renewal and pluripotency by mouse embryonic stem (mES) cells (Tamm, Bower et al. 2011). Briefly, a new path downstream of the LIF receptor was found with the activation of the Src kinase Yes, which in turn activated cytoplasmic Yes-associated protein (YAP) which would enter the nucleus and form a transcription complex with TEAD2, activating the transcription of other well described self-renewal and pluripotency factors such as Oct3/4 and Nanog (FIG. 1).

The present inventors have found that FBS can also activate TEAD2-dependent transcriptional activity. Through a set of fractionation techniques it was managed to identify one component in serum that activates the TEAD2-dependent transcription. The isolated protein was identified as a component of the Inter-alpha trypsin inhibitor (Iα) family: ITIH2 or IαI heavy chain 2 (HC2).

The IαI protein family is a complex group of protein-glycosaminoglycan-protein (PGP) complexes that occur constitutively at quite high concentrations in serum (0.6-1.2 mg/ml in humans) (Josic, Brown et al. 2006), as a results of alternate combinations of five kinds of heavy chains: HC1, HC2, HC3, HC4 and HC5 (although this last two have not been found to form complexes and have been only found in serum alone as peptides) and the kunitz-domain protease inhibitor Bikunin (Bk) linked together by a Chondroitin sulphate (CS) chain. The two most common members of the IαI protein family are IαI (HC1, HC2 and Bk) and Pre-α-inhibitor (PαI, HC3 and Bk); although IαIH2 (HC2, Bk), IαIH4P (only HC4) and Bk alone can also be found in plasma (FIG. 2).

The IαI proteins are mainly produced by the liver; the pro-peptides are processed and assembled in the Golgi and then secreted into the blood stream. The IαI protein complexes are still mostly inactive until they reach their target tissue and are cleaved by the tumour-necrosis factor gene-associated protein 6 (TSG-6). TSG-6 cleaves the HC covalent bond with the Chondroitin sulphate chain and forms a transient covalent bond with the HC to transfer it finally to hyaluronan (HA), a common part of the extra-cellular matrix. The bikunin domain increases in proteolytic activity in conjunction with TSG-6 (Wisniewski, Hua et al. 1996), and is solely responsible the protease inhibitory activity of IαI against trypsin, chymotrypsin, plasmin, cathepsin G, acrosin, and leukocyte elastase. Hyaluronan is a long, linear, non-sulphated glycosaminoglycan (GAG) made of the repeating disaccharide: (1-β-4)D-glucuronic acid and (1-β-3)N-acetyl-D-glucosamine. Hyaluronan has also been described as an important element in embryonic development (Schoenfelder and Einspanier 2003), tissue organization, (Trochon, Mabilat et al. 1996, Itano, Atsumi et al. 2002), wound healing (Pienimaki, Rilla et al. 2001, Baier Leach, Bivens et al. 2003), angiogenesis (West, Hampson et al. 1985), tumorigenesis (Toole and Hascall 2002), and possibly even in the biomechanical properties of tissues. In addition, it is well known that HA associates with cell-surface receptors and may help regulate cell motility and adhesion (Zhu, Mitsuhashi et al. 2006, Block, Hansen et al. 2011). The IαI-HCs have been the only proteins clearly demonstrated to bind covalently to HA. By binding the HA fibers in the tissues, the HCs can modify the niche of the cells and therefore play a role in e.g. adhesion, inflammation and ECM formation. Some studies suggest that IαI proteins not only have an important role in the control of inflammation and stabilization of the extracellular matrix, but could also induce the production and secretion of a HA-rich extracellular matrix when added to the cells.

Figure 4:
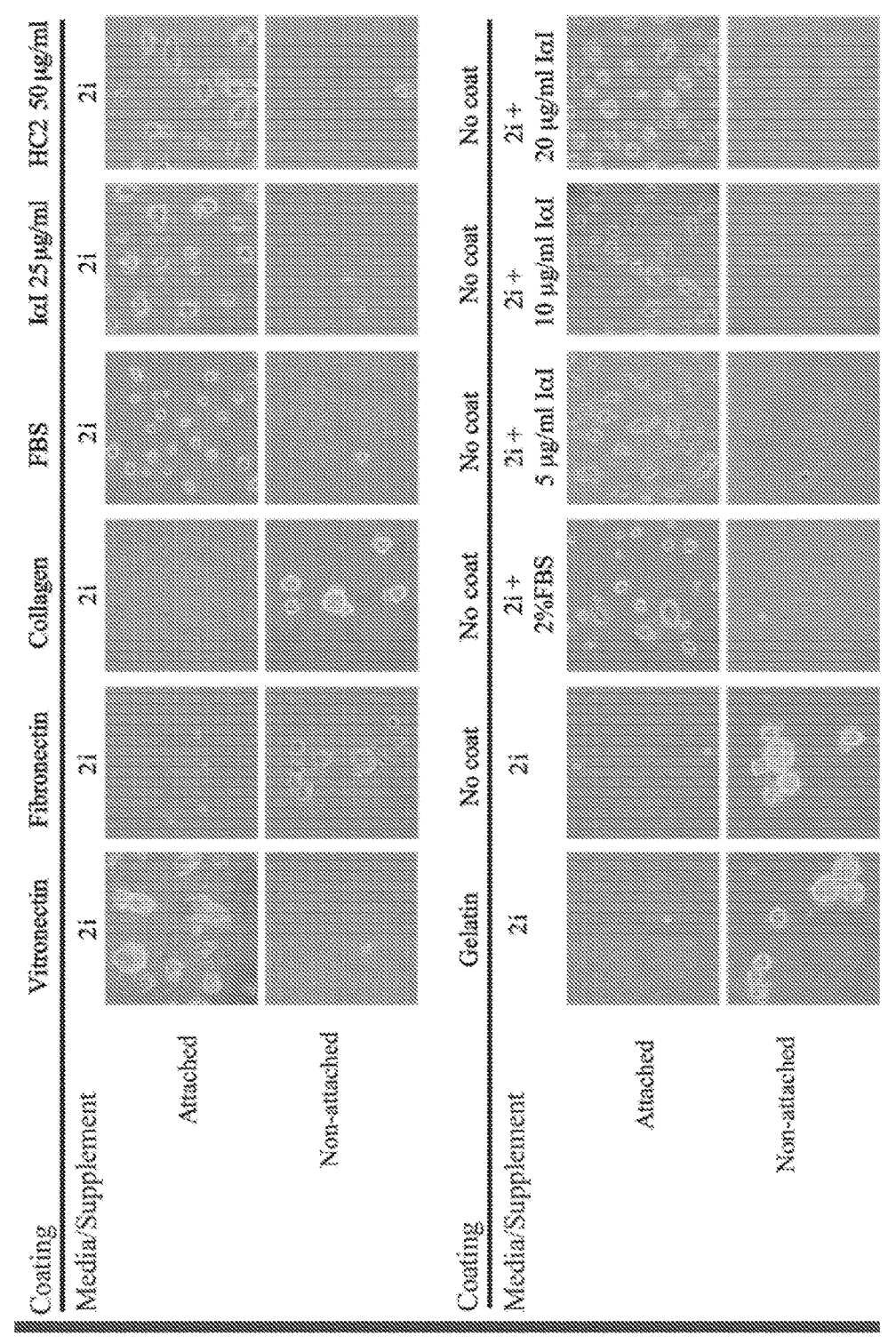
Figure 6:
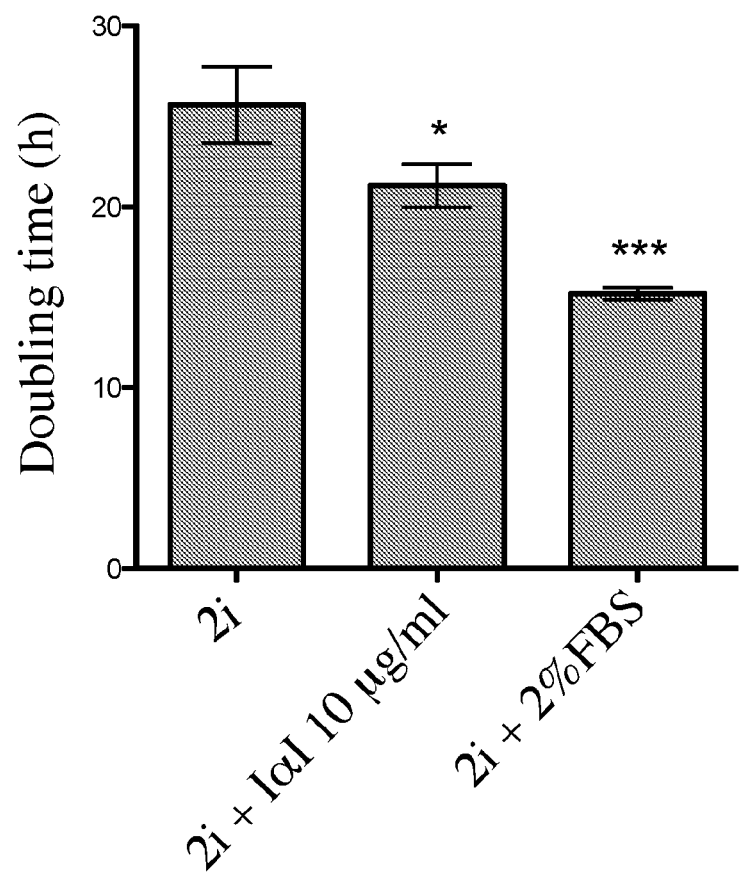
FIG. 6 shows the doublings times for mES cell line E14 grown for 3 passages in 2i media, 2i media supplemented with 2% FBS and 2i supplemented with IαI 10 μg/ml.

According to the present invention it has been found that IαI is important for PS cell culturing. When using the semi-defined media 2i, and the totally defined suspension media ESN2 with LIF and FGFb, mES cells grow in floating spheres and at a slower rate than in serum-containing conditions. Moreover, when the conventional coating surfaces gelatin, fibronectin and collagen were used, mouse ES cells in 2i or ESN2 media did not attach and continued growing as free floating spheres (FIG. 4). The addition of 2% FBS made the cells adhere to the plastic surface in nice tight colonies and accelerates the doubling time. In embodiments, the addition of the corresponding (10 µg/ml) or lower amounts of IαI also achieves adhesion of the mES colonies to the plastic surface in the serum-free 2i media, increasing the proliferation rate compared to 2i medium alone (FIGS. 4 and 6).

Four human PS cell lines were also tested for attachment when using a completely recombinant, serum-free media TeSR™-E8™. After one passage of E8 adaptation done step-wise from mTeSR™ 1 to TeSR™-E8™ (StemCell Technologies) the cells were seeded using different conditions. FIG. 4 shows attachment data on the human iPS cell line K02C. The negative control shows no attachment on non-coated plates when no supplementation is added to the commercial TeSR™-E8™ media, while they sit down on plastic dishes coated using a vitronectin peptide (Vitronectin FX™, StemCell Technologies). The human iPS cell line K02C also sits down on plastic dishes coated using 20 µg/ml IαI-HC2. Moreover, the supplementation of the media with a concentration ranging from 10 to 50 µg/ml of human, purified, complete molecule IαI also induced attachment of the human iPS cells on non-coated plastic dishes (FIG. 4). The human ES cell lines H181 and H207 (kindly provided by Dr. Outti Houvatta) and HUES1 (kindly provided by Dr. Douglas A. Melton) showed the same attachment behavior under the same conditions, and maintained pluripotency as well as colony morphology when cultured for over 5 passages in TeSR™-E8™ medium supplemented with 20 µg/ml IαI.

According to an embodiment of the present invention, IαI may form part of the ECM of PS cells and modify the properties or their niche, inducing extracellular matrix formation and/or remodeling. Also IαI may be added to defined cultures in order to promote attachment and provide a good environment for the cell survival and proliferation in vitro. IαI will bind to the cells, modifying the signaling from their environment and improving survival after splitting and maintenance of self-renewal and pluripotency.

EXAMPLES

Serum fractionation and Identification the active fractions in TEAD2-dependent transcription activation.

Fetal Bovine Serum (FBS) was first treated with a mild acetonitrile (ACN) precipitation to separate smaller proteins from its carriers as previously described (Lei et al, 2008). Briefly, the FBS was diluted with the addition of 30% V/V of ddH$_2$O and 20% V/V of acetonitrile (ACN) and warmed to 40° C. for 15 min. The mixture was then centrifuged at 14,000×g for 10 min to precipitate any insoluble material. The supernatant was diluted in binding buffer for a modified Blue Sepharose Chromatography purification, as described previously (Arakawa et al, 2007). Briefly, 4 ml of diluted FBS was further diluted with the addition of 4 ml of a Saturated Ammonium Sulphate solution (SAS) and 24 ml of Binding buffer (20 mM Phosphate Buffer, 2 M Ammonium sulphate, pH 7) before adding it to an equilibrated Blue Sepharose column (GE Healthcare). The column was subsequently washed with 20 mM Phosphate buffer pH 7 to remove all the bound Bovine Serum Albumin (BSA) and further eluted; first with 20 mM Phosphate buffer with 2 M NaCl pH 7 and then with 20 mM Phosphate buffer 1 M Arginine (Arg) pH 7.

The eluted fractions, Elution 1 and Elution 2, were concentrated and dialyzed against PBS using a Vivaspin 6 column (GE Healthcare) and then added to E14 mES cells in serum-free media and TEAD2-dependent transcription activity was assessed using a luciferase assay. E14 mES cell lines were seeded into 24 well plates in serum-containing media and Gelatin-coated plates and grown overnight until 70-80% confluence. The cells were then transfected using Lipofectamine™ 2000 (Life-Technologies) according to the manufacturer's recommendations, in OPTI-MEM serum-free media (Life Technologies) for 4 hours at 37° C. 5% $CO_2$ after which serum-free GMEM-based media was added to stop the transfection. The cells were transfected with pCS GT-IIC-luciferase (GTIIC) (Jiang and Eberhardt 1995) and the pCMV β-gal reference plasmid containing a bacterial β-galactosidase gene. After being serum-starved for 24 hours the cells were exposed to the different eluted fractions diluted into serum-free media and the TEAD2-dependent transcriptional activity was measured using a Luciferase assay. The cells were lysed and assayed for luciferase and β-galactosidase activities in a microplate luminometer and photometer reader (Wallac VICTOR 1420 Multilabel Counter: Perkin Elmer).

The first elution sample (2 M NaCl) was found to have the most TEAD2-dependent transcription activation effect (FIG. 3A) and was further fractionated using with a conventional Heparin Chromatography (Pharmacia AB, now GE Healthcare). Briefly, the eluted fraction was concentrated and dialyzed against the Heparin Chromatography binding buffer 50 mM Tris-HCl pH 8 using a Vivaspin column 20 (GE Healthcare) and loaded on to an equilibrated column. The elution was made step-wise with 6 fractions of 1 ml volume with 0.05-0.1-0.2-0.5-1-2 M NaCl. The fractions were again dyalized and concentrated using Vivaspin 6 columns into a cell-appropriate buffer and tested for TEAD2-dependent transcription as described above. The different eluted samples were analyzed using SDS-PAGE 10% acrylamide gel and Comassie Blue staining. The TEAD2-dependent transcription effect was compared to the protein patterns of the different fractions and two bands were identified as possible TEAD2-transcription activating molecules. The gel was sent for MS-MALDI-TOFF analysis (Åke Engstrom, IMBIM) and the bands were identified as 1) inter-alpha globulin inhibitor H2 polypeptide [Bos taurus] and 2) alpha-2-macroglobulin [Bos taurus].

Figure 3:
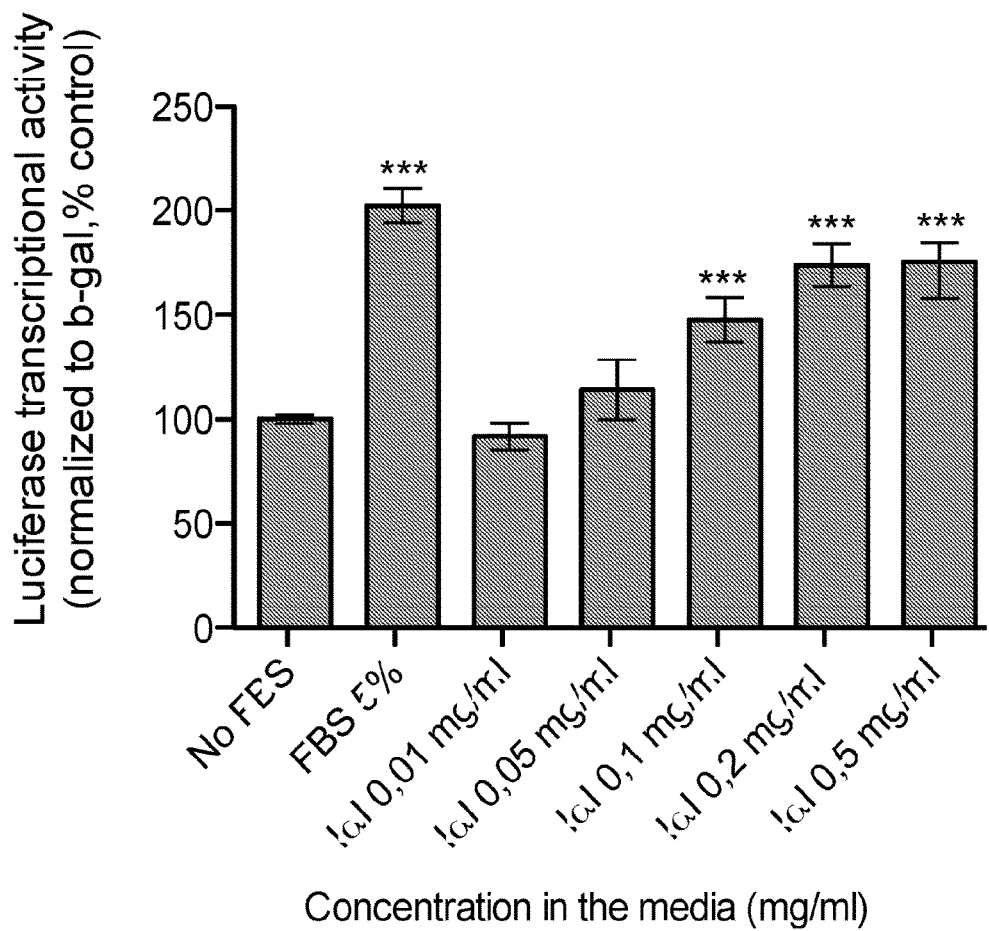
FIG. 3 shows a dose-response analysis of the effect of IαI on TEAD2-dependent transcription activity in mES cells.

Purified human IαI was tested on the cells as described above and a dose-response test was performed. IαI exposure on the cells not only had a TEAD2-transcriptional activation effect but this effect also followed a dose-response trend reaching similar amounts than 5% FBS Results are presented as the mean percentage of the control and SEM bars for at least three independent experiments made in triplicate and normalized to % of the control were the control is 100% for the serum-starved cells. Statistical analysis was done by One-way ANOVA with Dunnett's post test using GraphPad Prism version 5.00d for Mac (GraphPad Software, San Diego Calif. USA) where * represents p<0.05,  represents p<0.001 and * p<0.001 (FIG. 3).

Purification of Human IαI.

The isolation of IαI and the heavy chains HC1 and HC2 was made as described before (Blom, Morgelin et al. 1999). Briefly, a side fraction from the commercial production of factor IX was dialysed against Phosphate-buffered saline (PBS) and centrifuged for the removal of insoluble protein aggregates. This material was then filtered and subjected to gel filtration on a HiPrep 26/60 Sephacryl S-400 HR, which yielded more than 95% pure IαI. For the release of the heavy chains, 2 M NaOH was added to a solution of IαI of 1 mg/ml in PBS to give a final concentration of 0.05 M NaOH (Enghild, Thogersen et al. 1989). After 15 min at room temperature, Tris-HCl pH 8.0 was added to yield a final concentration of 0.25 M. The mixture was incubated for 1 hour at 37° C. The sample was then dialyzed against 20 mM sodium phosphate pH 7.6 overnight at 4° C., and applied to an anion exchange gel (MonoQ 5/50 GL; GE Healthcare) equilibrated with the same buffer. The proteins were eluted at a linear flow rate of 0.5 ml/min with 100 ml of a gradient from 0 to 0.7 M NaCl in 20 mM sodium phosphate, pH 7.6 (Balduyck, Piva et al. 1993). The fractions were analysed in 8% acrylamide SDS-PAGE gels followed by staining with Coomassie Brilliant Blue. Unless specified otherwise, protein concentrations were determined by UV measurements. The absorbance coefficients for the protein moieties of IαI, HC1 and HC2 were obtained from a former publication (Blom, Morgelin et al. 1999). The corresponding values for the whole proteins are 0.60, 0.47, and 0.72 $mg^{-1}$ ml $cm^{-1}$, for IαI, HC1 and HC2, respectively. The protein solutions were concentrated and dialyzed against PBS in Vivaspin 20 columns (GE Healthcare Bio-Sciences AB) and stored at −20° C. until they were used for experiments.

Addition of 2% FBS or 10 μg/ml IαI increases doubling time of mES cells in 2i media.

Figure 5:
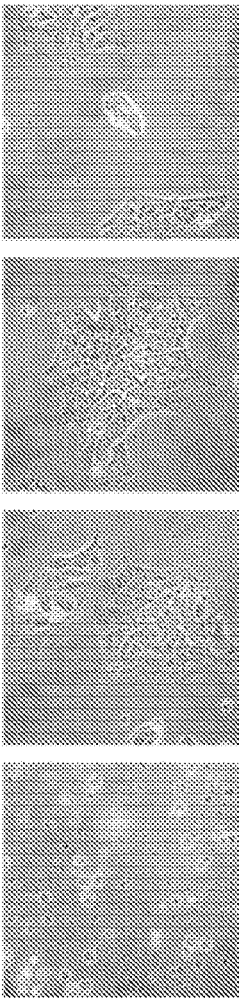
FIG. 5 shows attachment assay bright-field images of human iPS cell line K02C in E8 media on: non-coated plastic, plastic coated with a vitronectin peptide (Vitronectin XF™, StemCell Technologies) for 1 h at RT, non-coated plastic with a supplementation in the media of 10 μg/ml of IαI, and on plastic coated with 20 μg/ml of IαI-HC2 ON at 4° C.

The E14 mES cell line was maintained in continuous culture in 10% FBS and KOSR at 50/50 concentration in a GMEM-based media (Sigma) supplemented with Penicillin, Streptomycin, Glutamate, Pyruvate (all from Life technologies), β-Mercaptoethanol (Sigma) and LIF (Millipore), on 0.1% Gelatin (Sigma) coated cell culture dishes (Corning); as previously described (Smith, 1991). The cells were passaged under serum-free conditions using TrypLE™ (Life Technologies) into 2i Media (Ying, 2008 Nature), a N2B27 formulation with LIF, PD0325901 and CHIR99021 inhibitors (Selleckchem). After two passages all the cells were growing in floating spheres. The spheres were again passaged in serum-free conditions using TryPLE™ and then plated in 2i media, 2i media with 2% FBS and 2i media supplemented with 10 μg/ml of IαI. The cells were grown for 3 passages and counted in every passage to assess the proliferation rate. The supplemented media showed a higher proliferation rate than the cells grown in floating spheres with 2i media. The FBS supplemented media had the shortest doubling time with a mean of 15.19 hours. The IαI supplemented media had a longer doubling time of 21.16 hours but still shorter than the 25.64 hours of the floating spheres grown in 2i media (FIG. 5). Statistical analysis further confirmed the significant difference in growth rates of the different formulations.

Assessment of attachment of mES cells in 2i media on different conventional surface coating proteins for embryonic stem cells and media additives FBS or IαI.

The different coating proteins were diluted in PBS to final concentrations of 10 μg/ml Vitronectin, 10 μg/ml Fibronectin, 10 μg/ml Collagen I, 2% FBS, 25 μg/ml IαI and 50 μg/ml HC2. 12 well plate wells were coated with the different solutions for 2 hours at 37° C. 5% $CO_2$. The wells were washed with PBS, 3 times for the Vitronectin, Fibronectin, Collagen I and FBS, and washed once for IαI and HC2. The same number of E14 mES cells were seeded into the different coated wells after serum-free splitting in 2i media. After 48 hours the media was transferred to new wells and fresh media was added to the old well, pictures were taken of the remaining attached cells in the well (upper panel) and the floating cell spheres transferred with the supernatant (lower panel) to assess attachment (FIG. 4). Similarly, E14 mES cells were passaged from 2i media in serum-free conditions using TryPLE™ and transferred to 2i media with or without 2% FBS, 5 µg/ml IαI, 10 µg/ml IαI or 20 µg/ml IαI. Control cells were seeded in Gelatin-coated (0.1%) wells in 2i medium (FIG. 4). The cells were also allowed to grow for 24-48 hours and pictures were taken of the attached cells and the floating spheres in the supernatant. None of the conventional coatings promoted attachment of the E14 mES cells grown in 2i media i.e. Gelatin, fibronectin and collagen all failed as suitable coating proteins for the 2i media formulation for the mES cell line E14. Only vitronectin supported attachment and growth of the mES colonies. When adding 2% FBS as a coating solution or as a supplement to the 2i media almost all the cells attached to the cell culture plastic. When coating the plastic with IαI or the cleaved globular part HC2 the cells also attached in the 2i media. When adding the human purified IαI protein as a supplement to the 2i media the cells also attached to the cell culture media (FIG. 4).

Long-term culture of E14 mES cells in 2i media for 20 passages.

The E14 mES cell line grown in 2i media was passaged in serum-free conditions using TryPLE™ and then plated in 2i media, 2i media 2% FBS or 2i media with 10 µg/ml of IαI. The cells in the supplemented medias attached to the cell culture plastic while the control cells (2i media alone) continued to grow as floating spheres. The cells grown in 2i media with 2% FBS showed a high attachment ratio with an increased spreading of the cells on the plate. However, under these conditions some colonies lost the tight colony morphology typical for mES cell colonies. The cells grown in the IαI-supplemented media also attached to the plastic, but did not loose the tight colony morphology. The cultures were maintained for 20 consecutive passages with maintained self-renewal and very low levels of differentiation. To investigate whether the cells retained their pluripotency, they were let to form embryoid bodies in hanging drops (1600 cells/drop) for 4 days and then allowed to adhere to cell culture plastic and subsequently differentiate for 6 days. No difference in the amount of EB-outgrowths containing beating cardiomyocytes was seen between the different media formulations.

Attachment of human PS cell lines in E8 media on different coated/supplemented conditions with IαI and HC2.

The human induced pluripotent stem cells line K02C and the human ES cell lines H181, H207 (kindly provided by Dr. Outi Houvatta) and HUES1 (kindly provided by Dr. Douglas A. Melton) were routinely cultured on Matrigel® (BD Biosciences, hES-qualified matrix) and the mTERS1® (StemCell Technologies, defined media containing BSA). Stepwise media adaptation was used to adapt culture from mTeSR™ to TeSR™-E8™ media and the adapted cultures were seeded onto Vitronectin-FX™ coating and TeSR™-E8™ media (StemCell Technologies) before the experiment. Human PS cells grown in E8 media were treated with ROCKi Y27632 (StemCell Technologies) and passaged using a gentle dissociation solution (0.5 M EDTA pH 8.0) and a cell lifter to collect small size colonies, additional mechanical break up of the colonies was done pipetting with a P1000. The colonies were seeded on a 12 well plate with: non-coated surface, Vitronectin-coated surface (1 h at RT), IαI-HC2 coated surface (20 µg/ml in PBS ON at 4° C.) and on non-coated surfaces with 10 µg/ml IαI supplementation of E8 media added in the well. After 24 hours the media in the wells was changed and pictures were taken to assess cell attachment. The human PS cells did not attach to the non-coated surface. The positive control with vitronectin coating achieved normal levels of human PS cell attachment. The addition of IαI to the E8 media stimulated the attachment of the human PS cells to a similar extend as vitronectin coating. The IαI-HC2 coated wells achieved lower but still remarkable attachment of cells as compared to the vitronectin coating or the IαI supplemented media. (FIG. 5).

Long-term culture of human PS cells in TeSR™-E8™ media supplemented with IαI on non-coated plastic.

Figure 7:
FIG. 7 shows bright-field microscope images of the human PS cell line K02C adapted to growing in the minimal E8 media in two different conditions: Vitronectin coating (Vitronectin FX™, Stem Cell Technologies) for 16 passages, and on non-coated plastic supplemented with 20 μg/ml IαI for 14 passages.
Figure 7:
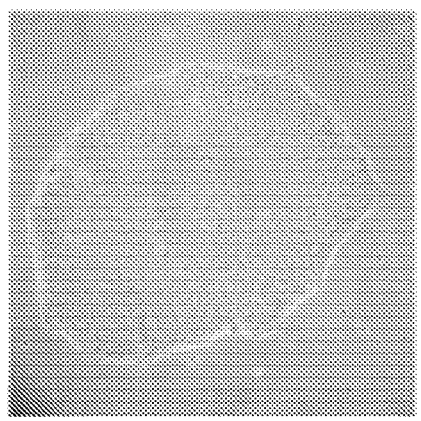

The human induced pluripotent stem cells line K02C and the human ES cell lines H181, H207 (kindly provided by Dr. Outi Houvatta) and HUES1 (kindly provided by Dr. Douglas A. Melton) were routinely cultured on Matrigel® (BD Biosciences, hES-qualified matrix) and the mTERS1® (StemCell Technologies, defined media containing BSA). Stepwise media adaptation was used to adapt culture from mTeSR™ to TeSR™-E8™ media and the adapted cultures were seeded onto Vitronectin-FX™ coating and TeSR™-E8™ media (StemCell Technologies). After one passage of adaptation of the human PS cells to TeSR™-E8™ and Vitronectin-FX™, the human PS cells were passaged using a gentle dissociation solution (0.5 M EDTA pH 8.0) and a cell lifter (TPP) to collect small size colonies. Part of the cells were then seeded onto non-coated plastic with TeSR™-E8™ supplemented with 20 µg/ml of purified IαI complete human protein. All four human PS cell lines showed attachment when seeded onto non-coated plastic with media supplemented with IαI. Cultures using both IαI supplementation or Vitronectin-FX™ coating were kept for long-term culture. The novel media formulation of TeSR™-E8™ supplemented with 20 µg/ml IαI maintained the human PS cells for over 20 passages in a similar manner as the commercial formulation of TeSR™-E8™ combined with Vitronectin-FX™ coating. FIG. 7 shows how the colonies keep the same morphology after 14 passages using IαI supplementation.

Immunocytochemistry of pluripotency markers.

The human PS cell lines adapted to grow on TeSR™-E8™ on Vitronectin-FX™ coating or 20 µg/ml IαI supplementation and the mouse ES cells adapted to grow on 2i media supplemented with 2% FBS or 10 µg/ml IαI were checked for pluripotency markers using immunocytochemistry and Alkaline phosphatase staining Oct3/4, Nanog, Sox2 were checked on mouse ES cells using immunocytochemistry. Both culture conditions show high levels of pluripotency markers with negligible or no signs of differentiation. The human PS cell lines K02C and H181 were checked using immunocytochemistry for the extracellular pluripotency markers Tra-1-60, Tra-1-80 and SSEA-4 alone or in combination with antibodies against IαI-HC1 and HC2. Both culture conditions maintained pluripotency marker expression on both cell lines. Moreover, IαI-HC2 showed a pattern similar to the pluripotency markers, being only positive on colonies also positive for pluripotency markers and not staining colonies that had started differentiation. In conclusion, addition of IαI to the media maintains pluripotency on serum free cultures on both mouse and human PS cells after 5 passages.

Alkaline-Phosphatase staining.

Figure 8:
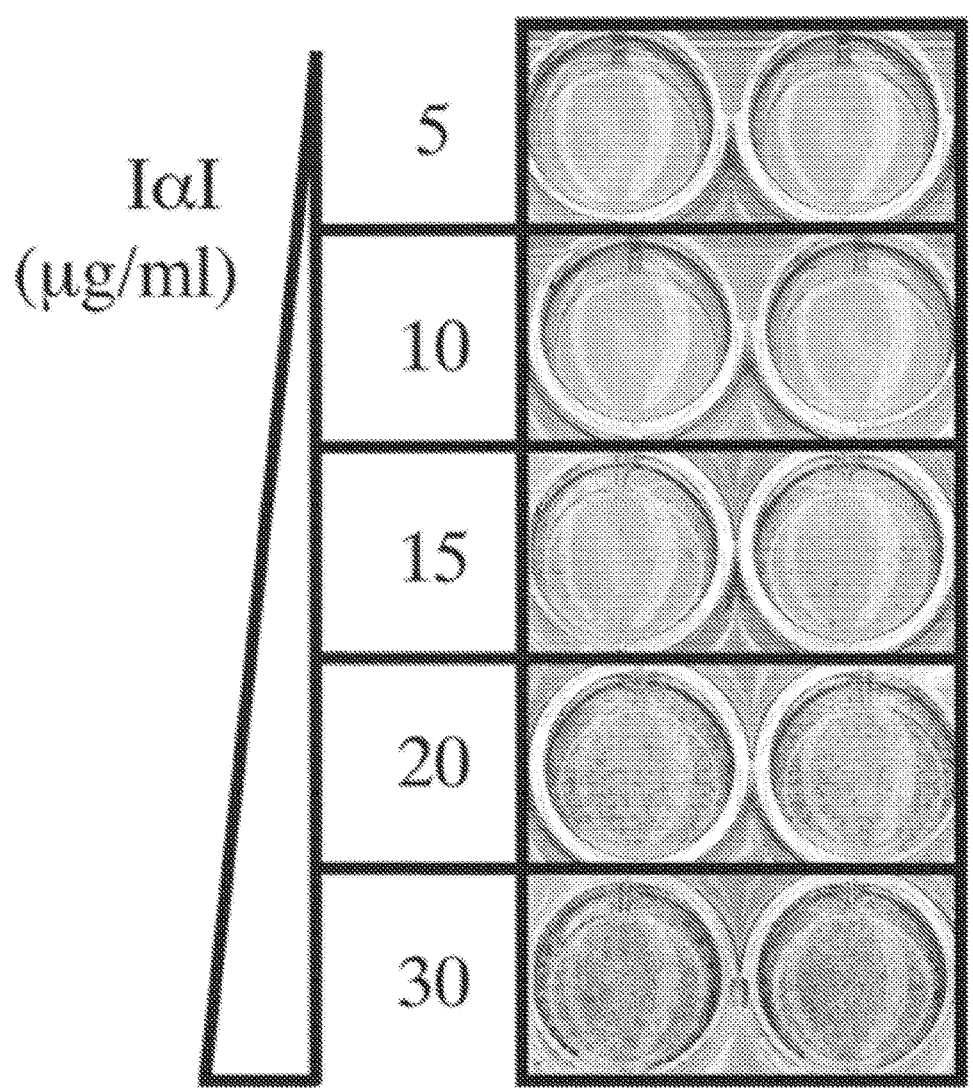
FIG. 8 shows alkaline phosphatase positive K02C hiPS cell colonies attached onto non-coated plastic wells using increasing concentrations of IαI in TeSR™-E8™ media three days after seeding.

The human PS cell lines H181 and K02C adapted to grow on TeSR™-E8™ and Vitronectin-FX™ coating were seeded using 0.5 EDTA pH 8.0 and a cell lifter and small colonies were seeded on a 12 well plate using TeSR™-E8™ media supplemented with different concentrations of human purified IαI complete protein. After two or three days of growing the cells were stained using an Alkaline Phosphatase kit (Life Technologies) in order to visually detect the pluripotent human PS colonies. Higher concentration of IαI achieved higher attachment and growth rates of the human ES cells (FIG. 8).

What is claimed is:

1. A cell free medium for at least one of seeding and culturing stem or progenitor cells on an uncoated surface, the medium comprising a partially or a completely chemically defined cell culture medium which comprises or is supplemented at a concentration of 2 µg/mL-100 µg/mL of one or more inter alpha trypsin inhibitor (IαI) proteins to promote adhesion of said cells to said uncoated surface during the first passage as well as self-renewal of said cells,
wherein the one or more IαI proteins are selected from the group consisting of an IαI protein comprising heavy chain 1 (HC1), heavy chain 2 (HC2), and bikunin (B) (IαI-HC1, HC2, B), an isolated heavy chain 2 (isolated HC2), and an IαI protein comprising heavy chain 2 (IαI-HC2), and
wherein the medium is whole serum free, serum component free and feeder cell free.

2. The medium of claim 1, wherein the completely chemically defined medium is E8.

3. The medium of claim 1, wherein the concentration of the one or more IαI proteins of IαI protein family is 10 µg/mL-50 µg/mL.

4. The medium of claim 1, wherein the one or more IαI proteins are un-complexed proteins isolated from serum or a serum fraction, produced as a recombinant protein, synthesized chemically, or a combination thereof.

5. The medium of claim 1, wherein the one or more IαI proteins comprise isolated HC2.

6. The medium of claim 1, further comprising Rho-associated kinase inhibitor (ROCKi).

7. The medium of claim 1, wherein the partially chemically defined medium is 2i medium.

8. A cell free medium for at least one of seeding and culturing stem or progenitor cells on an uncoated surface, the medium comprising a partially or a completely chemically defined cell culture medium which comprises or is supplemented at a concentration of 2 µg/mL-100 µg/mL of an IαI-HC1, HC2, B to promote adhesion of said cells to said uncoated surface during the first passage as well as self-renewal of said cells,
wherein the medium is whole serum free, serum component free and feeder cell free.

9. The medium of claim 8, wherein the completely chemically defined medium is E8.

10. The medium of claim 8, wherein the concentration of the IαI protein is 10 µg/mL-50 µg/mL.

11. The medium of claim 8, wherein the IαI protein is an un-complexed protein isolated from serum or a serum fraction, produced as a recombinant protein, synthesized chemically, or a combination thereof.

12. The medium of claim 8, further comprising Rho-associated kinase inhibitor (ROCKi).

13. The medium of claim 8, wherein the partially chemically defined medium is 2i medium.

14. A cell free medium for at least one of seeding and culturing stem or progenitor cells on an uncoated surface, the medium comprising a partially or completely chemically defined cell culture medium and comprises or is being supplemented at a concentration of 2 µg/mL-100 µg/mL with an inter alpha trypsin inhibitor (IαI) protein that comprises heavy chain 2 (IαI-HC2) to promote adhesion of said cells to said uncoated surface during the first passage as well as self-renewal of said cells,
wherein the medium is whole serum free, serum component free and feeder cell free.

15. The medium of claim 14, wherein the completely chemically defined medium is E8.

16. The medium of claim 14, wherein the concentration of the IαI protein is 10 µg/mL-50 µg/mL.

17. The medium of claim 14, wherein the IαI-HC2 is un-complexed proteins isolated from serum or a serum fraction, produced as a recombinant protein, synthesized chemically, or a combination thereof.

18. The medium of claim 14, wherein said medium is used on an uncoated surface.

19. The medium of claim 14, further comprising Rho-associated kinase inhibitor (ROCKi).

20. The medium of claim 14, wherein the partially chemically defined medium is 2i medium.

* * * * *